United States Patent
Poppe et al.

(10) Patent No.: US 11,845,706 B2
(45) Date of Patent: Dec. 19, 2023

(54) METHOD AND PLANT FOR PREPARING VINYL CHLORIDE FROM 1,2-DICHLOROETHANE

(71) Applicants: THYSSENKRUPP AG, Essen (DE); THYSSENKRUPP INDUSTRIAL SOLUTIONS AG, Essen (DE); WESTLAKE VINNOLIT GMBH & CO. KG, Burgkirchen (DE)

(72) Inventors: Alexander Poppe, Frankfurt (DE); Peter Kammerhofer, Burgkirchen (DE); Klaus Krejci, Burghausen (DE)

(73) Assignees: Westlake Vinnolit GmbH & Co. KG, Burgkirchen (DE); Thyssenkrupp AG, Essen (DE); Thysenkrupp Industrial Solutions AG, Essen (DE)

( * ) Notice: Subject to any disclaimer, the term of this patent is extended or adjusted under 35 U.S.C. 154(b) by 102 days.

(21) Appl. No.: 17/607,262

(22) PCT Filed: Apr. 22, 2020

(86) PCT No.: PCT/EP2020/061203
§ 371 (c)(1),
(2) Date: Oct. 28, 2021

(87) PCT Pub. No.: WO2020/221640
PCT Pub. Date: Nov. 5, 2020

(65) Prior Publication Data
US 2022/0227690 A1    Jul. 21, 2022

(30) Foreign Application Priority Data

Apr. 30, 2019   (DE) .................... 10 2019 206 154.0

(51) Int. Cl.
*C07C 17/25* (2006.01)
*B01J 19/24* (2006.01)

(52) U.S. Cl.
CPC ............ *C07C 17/25* (2013.01); *B01J 19/2415* (2013.01); *B01J 2219/00092* (2013.01); *B01J 2219/00094* (2013.01); *B01J 2219/00157* (2013.01)

(58) Field of Classification Search
CPC ................................. C07C 17/25; C07C 21/06
See application file for complete search history.

(56) References Cited

U.S. PATENT DOCUMENTS

| 4,746,759 A | 5/1988 | Dummer et al. |
| 4,798,914 A | 1/1989 | Link et al. |

(Continued)

FOREIGN PATENT DOCUMENTS

| DE | 1 468 827 A1 | 12/1969 |
| EP | 0 002 021 A1 | 5/1979 |

(Continued)

OTHER PUBLICATIONS

European Patent Office, International Search Report in International Application No. PCT/EP2020/061203 (dated Jul. 16, 2020).

(Continued)

*Primary Examiner* — Jafar F Parsa
(74) *Attorney, Agent, or Firm* — Leydig, Voit & Mayer, Ltd.

(57) ABSTRACT

Disclosed is a method for preparing vinyl chloride by catalytic thermal cracking of 1,2-dichloroethane, in which method the heat required for the thermal cracking is supplied via a liquid or condensing heat transfer medium, wherein, the heat transfer medium is heated at least in part by means of waste heat from a plant for combusting liquid and/or gaseous residues of a chemical plant. The invention also relates to a plant for preparing vinyl chloride by catalytic thermal cracking of 1,2-dichloroethane. The heat required for thermal cracking can be obtained from cheaply available (Continued)

waste heat. For example, it is possible to temporarily heat the heat transfer medium exclusively by means of the second heating device operated by waste heat, wherein said waste heat can, for example, be waste heat from a plant for preparing vinyl chloride.

15 Claims, 1 Drawing Sheet

(56) References Cited

U.S. PATENT DOCUMENTS

| | | | |
|---|---|---|---|
| 9,334,209 | B2 | 5/2016 | Braun |
| 2015/0353452 | A1 | 12/2015 | Braun |

FOREIGN PATENT DOCUMENTS

| | | | | |
|---|---|---|---|---|
| EP | 0 225 617 A1 | 6/1987 | | |
| EP | 0 264 065 A1 | 4/1988 | | |
| EP | 2712857 A1 * | 4/2014 | ............... | C07C 1/24 |
| WO | WO 2014/108159 A1 | 7/2014 | | |

OTHER PUBLICATIONS

European Patent Office, Written Opinion in International Application No. PCT/EP2020/061203 (dated Jul. 16, 2020).
International Bureau of WIPO, International Preliminary Report on Patentability in International Application No. PCT/EP2020/061203 (dated Nov. 2, 2021).
U.S. Appl. No. 17/607,096, filed Oct. 28, 2021.

\* cited by examiner

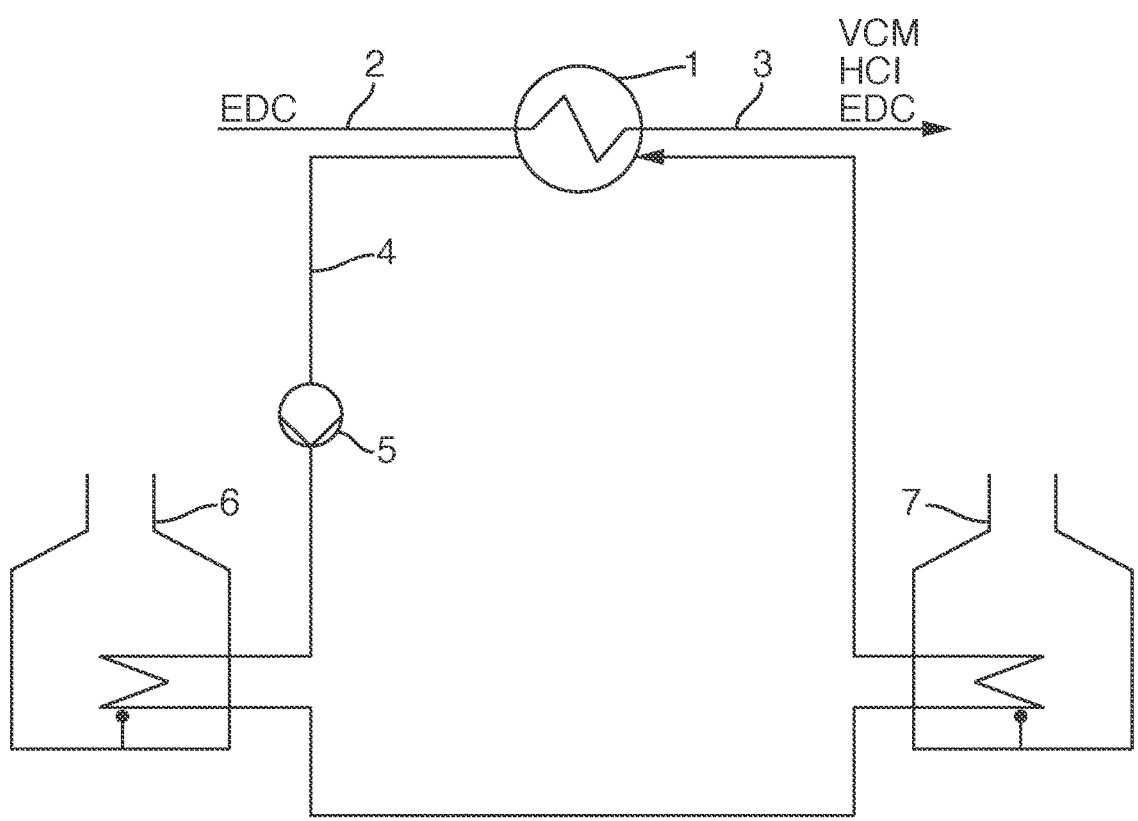

METHOD AND PLANT FOR PREPARING VINYL CHLORIDE FROM 1,2-DICHLOROETHANE

CROSS-REFERENCE TO RELATED APPLICATIONS

This patent application is the U.S. national phase of International Application No. PCT/EP2020/061203, filed on Apr. 22, 2020, which claims the benefit of German Patent Application No. 10 2019 206 154.0, filed Apr. 30, 2019, the disclosures of which are incorporated herein by reference in their entireties for all purposes.

The present invention relates to a method for producing vinyl chloride by catalytic thermal cleavage of 1,2-dichloroethane, in which the heat required for the thermal cleavage is supplied via a liquid or condensing heat transfer medium. The subject matter of the present invention is further a plant for producing vinyl chloride by catalytic thermal cleavage of 1,2-dichloroethane, in which the heat required for thermal cleavage is supplied via a liquid or condensing heat transfer medium, comprising at least one reactor in which the thermal cleavage takes place and at least one first heating device, by means of which the reaction medium is heated in the reactor by means of the heat transfer medium.

The thermal cleavage of 1,2-dichloroethane for producing vinyl chloride, which is required particularly for producing polyvinyl chloride, follows the reaction equation (1) shown below:

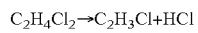

$$C_2H_4Cl_2 \rightarrow C_2H_3Cl + HCl$$

It is an endothermic reaction wherein the pyrolysis can be carried out either without a catalyst in the gas phase under high pressure of 1 to 3 MPa and at a temperature of 450 to 600° C. or also in catalytic methods that allow the pyrolysis to occur lower temperatures.

PRIOR ART

For example, a method for producing vinyl chloride by thermal cleavage of 1,2-dichloroethane is described in EP 264 065 A1, in which 1,2-dichloroethane is heated in a first container, then transferred to a second container in which it is evaporated without further heating under lower pressure than in the first container and the gaseous 1,2-dichloroethane is fed into a cracking furnace, in which the cleavage to vinyl chloride and hydrogen chloride takes place. The temperature of the 1,2-dichloroethane is 220° C. to 280° C. when it leaves the second container. In the cracking furnace, pipes in which the 1,2-dichloroethane is thermally cleaved are heated by means of a fossil fuel. The gaseous 1,2-dichloroethane is heated to 525° C. or 533° C. in the radiation zone of the cracking furnace.

EP 264 065 A1 also mentions that a temperature control medium can be used to preheat the liquid, fresh 1,2-dichloroethane, which temperature control medium in turn is heated in the convection zone of the cracking furnace with the flue gas produced by the burners heating the cracking furnace. Heated, high-boiling liquids such as mineral oil, silicone oil or molten diphenyl are suitable as the temperature control medium. However, only preheating to a temperature of 150 to 220° C. takes place in this way, while the pyrolysis takes place even at temperatures of around 530° C. In this known method, there is therefore no provision for the pyrolysis to be carried out at temperatures in the range from 300 to 400° C. and for all the necessary heating to be carried out with the aid of a liquid heat transfer medium.

As a rule, a plant complex for producing vinyl chloride consists of
- a plant for producing 1,2-dichloroethane from ethene and chlorine ("direct chlorination"), or
- a plant for producing 1,2-dichloroethane from ethene, hydrogen chloride and oxygen ("oxychlorination"),
- a plant for the purification of 1,2-dichloroethane by distillation,
- a plant for the thermal cleavage of the 1,2-dichloroethane purified by distillation to vinyl chloride and hydrogen chloride and
- a plant for the distillative separation of the hydrogen chloride and unconverted 1,2-dichloroethane and for the purification of the vinyl chloride.

The hydrogen chloride obtained by thermal cleavage of the 1,2-dichloroethane can be returned to the oxychlorination plant, where it can be reacted again with ethene and oxygen to form 1,2-dichloroethane.

Furthermore, the plant complex described above can comprise a plant for the combustion of liquid and/or gaseous chlorinated hydrocarbons. The latter occur as by-products in the process of producing vinyl chloride and are mainly separated off from 1,2-dichloroethane in the purification by distillation. The hydrogen chloride produced during the combustion of these substances is either given off to other production processes as aqueous hydrochloric acid or also returned to the oxychlorination plant. Existing methods use the waste heat from combustion to generate steam.

In the method described in DE 102 52 891 A1 for the cleavage of 1,2-dichloroethane into vinyl chloride and hydrogen chloride, a catalyst is used which allows the operating temperature to be reduced during the endothermic cleavage. However, in this method too, the tubular reactor is fired with a primary energy source such as oil or gas, wherein the furnace is divided into a radiation zone and a convection zone. In the radiation zone, the heat required for pyrolysis is mainly transferred to the reaction tube by radiation from the furnace walls, which are heated by the burner. In the convection zone, the energy content of the hot flue gases emerging from the radiation zone is used by convective heat transfer, whereby the 1,2-dichloroethane as the starting material of the pyrolysis reaction can be preheated, evaporated or overheated.

Various measures for saving energy and/or heat recovery in plants for producing 1,2-dichloroethane are known from the prior art. Such measures lead to a significant reduction in operating costs and thus make a significant contribution to the profitability of the plant and to a reduction in the $CO_2$ emissions of the plant. These are, for example, measures that use the heat of reaction from the exothermic reaction steps to heat sinks in the process. WO 2014/108159 A1 lists various known measures for heat recovery in plants for producing vinyl chloride and names the corresponding literature references.

EP 0 225 617 A1 describes a method for producing vinyl chloride by thermal cleavage of 1,2-dichloroethane, wherein it is mentioned that when this method is carried out, in some cases, a recovery of waste heat from the flue gases of a cracking furnace firing is provided with the generation of water vapor. However, such methods are not very economical because of the relatively low flue gas temperature. The thermal cleavage of 1,2-dichloroethane also takes place in this method at comparatively high temperatures. First, the starting material is preheated to about 243° C., then evaporated partly by relaxation and partly by applying steam and then thermally cleaved in a cracking furnace at temperatures between 435° C. and 497° C. without the use of a catalyst.

Heating by means of a heat transfer oil is not provided and also not possible at these temperatures.

EP 0 002 021 A1 describes a method for the catalytic dehydrohalogenation of 1,2-dichloroethane to vinyl chloride in which zeolitic catalysts which have been treated with a Lewis acid are used. When using such catalysts, it is possible to carry out the reaction at elevated pressure and temperatures in the range from 200° C. to 400° C. and thus considerably lower temperatures than in the conventional pyrolysis of 1,2-dichloroethane.

The object of the present invention is to provide an improved method for producing vinyl chloride by thermal cleavage of 1,2-dichloroethane, in which a reduction in operating costs is achieved.

The solution to the aforementioned problem is provided by a method for producing vinyl chloride by catalytic thermal cleavage of 1,2-dichloroethane of the type mentioned above and the features described herein.

According to the invention, the liquid or condensing heat transfer medium is heated at least temporarily and/or at least partially or completely by means of the waste heat from a plant for the incineration of liquid and/or gaseous residues of a chemical plant. This creates the possibility of at least temporarily making available the heat required for the thermal cleavage from inexpensive waste heat. Using catalysts for the thermal cleavage of 1,2-dichloroethane can shift the temperature range in which the reaction takes place to lower temperatures, particularly in the range from about 200° C. to about 400° C., so that the reactor can be heated by means of a heat transfer medium instead of direct firing with fossil fuels as was previously the case. Instead of a cracking tube furnace, for example, a tube bundle heat exchanger can be used as the reactor, in which heat exchanger the tubes are filled with catalyst and the heat transfer medium flows through the jacket space, preferably in a circuit.

According to a preferred further development of the method according to the invention, the heat required for the reaction is made available at least temporarily and/or at least partially by heating the heat transfer medium by means of the waste heat from a chemical plant. This preferred variant of the method provides that the heat required for the reaction is generally made available via a first heating device which can be heated by means of fossil fuels, for example, but a second heating device operated via waste heat that can be used at least temporarily is present. In these cases, the first heating device can be throttled or, possible, shut down completely for a certain period of time, or the heat transfer medium can be guided such that it bypasses the first heating device in terms of flow.

According to a preferred further development of the method according to the invention, the heat required for the reaction is at least temporarily made available by means of the waste heat from a plant for the incineration of liquid and/or gaseous chlorinated hydrocarbons, such as those obtained as by-products in a plant for producing vinyl chloride.

According to a preferred further development of the method according to the invention, the liquid or condensing heat transfer medium is heated at least temporarily partly by the combustion of at least one fuel and partly by heating using the waste heat from a chemical plant. The use of a liquid or condensing heat transfer medium to provide all of the heat of reaction that is required for the pyrolytic cleavage of 1,2-dichloroethane is made possible by carrying out the reaction in the presence of suitable catalysts, which enable the reaction temperature to be reduced significantly compared to conventional methods without catalysis. When using such catalysts, the reaction can be reduced, for example, from the temperatures customary in conventional methods in the order of magnitude of about 430° C. to about 530° C. to temperatures in the range of particularly about 200° C. to 400° C. Heating to temperatures in this range is possible, for example, when using a heat transfer oil or, possibly, a molten salt. Substances such as those mentioned in the above-mentioned EP 0 002 021 A1 can be considered as a catalyst.

A method for purely thermal (uncatalyzed in a pyrolysis furnace) or thermal-catalytic EDC cleavage (with the supply of heat when using a catalyst) usually consists of the sub-steps:

preheating of liquid 1,2-dichloroethane up to the evaporation temperature at the given pressure evaporating the preheated 1,2-dichloroethane if necessary, overheating of the vaporous 1,2-dichloroethane up to the range of the reaction temperature (if the previous evaporation did not take place in the range of the reaction temperature)

cleavage reaction (purely thermal or thermal using a catalyst) with the supply of heat.

The subject matter of the invention is a method which, in addition to heating the catalytic-thermal cleavage reaction by a liquid or condensing heat transfer medium, also enables the upstream preheating, evaporation or overheating of the 1,2-dichloroethane to be heated by this heat transfer medium. Not all of these steps have to be heated by means of the heat transfer medium. The method according to the invention comprises the heating of at least one up to any combination of the above-mentioned sub-steps, wherein it is possible for the individual sub-steps in turn to be subdivided (in terms of apparatus) into individual steps.

"Heating" in the context of the method according to the invention means the transfer of heat to the starting material 1,2-dichloroethane and/or the reaction mixture by means of a heat transfer medium. The starting material 1,2-dichloroethane can be heated, evaporated or overheated. The reaction mixture in the reactor can be supplied with heat at a constant temperature level (isothermal reaction procedure). The reaction mixture can also heat up further, wherein the heat supplied by the heating is used partly to cover the heat requirement for the reaction and partly to further heat the reaction mixture. Finally, the heat supply to the reaction mixture can be adjusted by heating so that the sensible heat content of the reaction mixture is at least partially used to cover the reaction heat requirement and the reaction mixture cools down in the reactor compared to the reactor inlet temperature. The heating and also the transfer of heat to the starting material 1,2-dichloroethane is carried out by a liquid heat transfer medium while cooling the heat transfer medium or reducing its sensible heat content and/or by a condensing heat transfer medium that was previously evaporated by means of a heating device.

Heating devices for the heat transfer medium in the context of the method according to the invention are, on the one hand, devices (heaters and/or evaporators or devices in which a heater and an evaporator function are combined) that can be heated by means of a fossil fuel such as heating oil or preferably natural gas. On the other hand, these are heat transfer devices (heaters and/or evaporators or devices in which a heater and an evaporator function are combined) that are heated by means of the waste heat from a plant for the incineration of by-products of a chemical plant, preferably a plant for the incineration of by-products of a plant complex for producing vinyl chloride. Such devices are known to those skilled in the art.

According to a preferred further development of the method according to the invention, at least one first heating device operated by combustion of at least one fuel and additionally at least one second heating device operated via the waste heat from a plant for the incineration of by-products of a chemical plant are used to heat the liquid or condensing heat transfer medium.

The heat demand of a plant for the catalytic-thermal cracking of 1,2-dichloroethane can usually only be partially covered by the combustion of by-products of the plant complex for producing vinyl chloride. In a preferred mode of operation, the heat transfer medium is therefore initially heated by means of the waste heat from the combustion of by-products and the remaining amount of heat required is supplied by the burning of a fossil fuel in a second heating system.

According to a preferred further development of the method according to the invention, the liquid or condensing heat transfer medium is conducted in a circuit and the at least one first heating device operated via burning of a fossil fuel and the at least one second heating device operated via waste heat are integrated into this circuit.

According to a preferred further development of the method according to the invention, at least one first heating device and at least one second heating device operated using waste heat are connected in series in the circuit. The heat transfer medium then flows in a line circuit first through the second heating device operated by waste heat and then downstream of this the first heating device or, however, these two heating devices are flowed through in reverse order. As an alternative to this, it is also possible to arrange the two heating devices in parallel, as it were, that is, the line circuit in which the heating devices are integrated is connected and the corresponding lines can be shut off, for example, via valves, so that the heat transfer medium can flow through the second heating device without said heat transfer medium also flowing through the first heating device and possibly vice versa.

According to a preferred further development of the method according to the invention, the heat transfer medium is conveyed in a circuit in which a reactor is integrated, in which the catalytic thermal cleavage of 1,2-dichloroethane is carried out, wherein there is a heat exchange between the reaction medium of the reactor and the heat transfer medium.

According to a preferred further development of the method according to the invention, the heat transfer medium is conveyed in the circuit in countercurrent to the flow of the reaction medium through the reactor. This variant is advantageous for effective heat transfer. As an alternative to this, however, a flow of the heat transfer medium in co-current with the flow of the reaction medium is also possible.

According to a preferred further development of the method according to the invention, the second heating device operated via waste heat is operated at least temporarily by means of the waste heat from a plant for the incineration of the by-products of a plant for producing vinyl chloride. This variant has the advantage that the waste heat is used, as it were, from a part of the plant of the same plant complex, thus improving the energy balance of the method.

According to a preferred further development of the method according to the invention, the second heating device operated via waste heat is operated permanently at full load. The remainder of the energy required for thermal cleavage can be supplied to the heat transfer medium by a heating plant heated by means of fossil fuels. In this variant of the method, it is provided that the second heating device operated via waste heat is preferably permanently at operating temperature.

According to a preferred further development of the method according to the invention, the thermal cleavage of 1,2-dichloroethane is carried out in a temperature range from 200° C. to 400° C. This is a preferred temperature range which can be easily implemented using liquid heat transfer media, for example, heat transfer oils.

The subject matter of the present invention is further a plant for producing vinyl chloride by catalytic thermal cleavage of 1,2-dichloroethane, in which preferably the heat required for preheating, evaporation and overheating and for the thermal cleavage of 1,2-dichloroethane is supplied via a liquid or condensing heat transfer medium, comprising at least one reactor in which the thermal cleavage takes place and at least one first heating device by means of which the reaction medium in the reactor is heated by means of the liquid heat transfer medium, wherein the plant according to the invention also comprises at least one second heating device operated via waste heat for heating the reaction medium. In this case, it is preferred that the heat transfer medium first flows through the second heating device operated using waste heat. The remainder of the heat required for cleaving the 1,2-dichloroethane, but also for preheating it in order to vaporize and/or overheat it, can be supplied by a heating system heated by means of fossil fuels.

A preferred development of the invention provides that the reactor is integrated into a circuit of the heat transfer medium, wherein at least the second heating device operated via waste heat is also integrated into the circuit.

According to a preferred variant of the invention, at least one first heating device operated via fuel and furthermore at least one second heating device operated via waste heat are integrated into the circuit of the heat transfer medium. In this case, the sequence of the flow is preferably such that the flow is first through the second heating device. The terms "first" or "second" heating device used here thus only designate the functionally different type of heating device, but do not specify the order in which the heat transfer medium flows through.

According to a preferred variant of the invention, the circuit of the heat transfer medium comprises a pump integrated into a line system, at least one first heating device operated via a fuel, at least one second heating device operated via waste heat and the reactor, wherein means for transferring heat from the heat transfer medium to a reaction medium flowing through the reactor or located in the reactor are provided.

A preferred further development of the invention provides that the first heating device operated via fuel and the second heating device operated via waste heat are arranged in series or, alternatively, in parallel in the circuit of the heat transfer medium.

A preferred further development of the invention provides that the reactor comprises a tube bundle heat exchanger, the tubes of which are filled with a catalyst and which preferably has jacket space through which the heat transfer medium flows in a circuit.

BRIEF DESCRIPTION OF THE DRAWING

The present invention is described in more detail below using an exemplary embodiment with reference to the accompanying drawing.

Shown are:

The FIGURE illustrates a schematically simplified plant scheme of a plant according to the invention for producing vinyl chloride by catalytic thermal cleavage from 1,2-dichloroethane.

DETAILED DESCRIPTION OF THE INVENTION

Reference is made below to the FIGURE and an exemplary embodiment variant of the method according to the invention is explained in more detail on the basis of this. The representation according to the FIGURE is greatly simplified schematically and only those plant components are shown which are of importance in the context of the present invention. The plant comprises a reactor 1, to which a reactor inlet flow of 1,2-dichloroethane (EDC) is supplied, for example, via at least one line 2, which 1,2-dichloroethane is pyrolyzed in the reactor 1 under the action of heat to form monomeric vinyl chloride (VCM), wherein hydrogen chloride is formed in addition to the vinyl chloride. The named products of the method leave the reactor 1 in a reactor outlet flow 3.

The reactor 1 is integrated into a circuit flow 4 of a heat transfer medium such that heat is supplied to the reactor via the liquid heat transfer medium, for example, a heat transfer oil, which preferably flows in countercurrent to the reaction medium, in order to heat the reaction medium flowing through the reactor to a temperature of, for example, 300° C. to 400° C., at which the catalytic thermal cleavage of 1,2-dichloroethane to vinyl chloride takes place in reactor 1.

The circuit flow 4 of the heat transfer medium is explained in more detail below. The line circuit 4 of the heat transfer medium comprises a pump 5 to convey the heat transfer medium in the circuit, wherein this first flows through a first heating device 6 downstream of the pump 5, which first heating device is fired with a fossil fuel, for example, in order to heat the heat transfer medium. After that, the heat transfer medium 4 flows through a second heating device 7, in which the heat transfer medium, if the second heating device 7 is in operation, can be heated with the aid of thermal energy from the waste heat from a chemical plant, for example, from a plant for producing vinyl chloride.

In the embodiment, the first heating device 6 and the second heating device 7 are arranged one behind the other in the flow direction in the line system of the heat transfer medium circuit flow 4 and are thus connected in series. As an alternative to this, however, both heating devices can also be connected in parallel to one another, that is, different from what is shown in the FIGURE, the two heating devices are integrated into a line system such that the heat transfer medium can flow through at least only one of the two heating devices, bypassing the respective other heating device.

In the variant shown in the FIGURE, with the arrangement of both heating devices in series and also in the variant not shown with parallel connection, valves not shown in the FIGURE can be provided to switch the heating devices on and off or to shut off the lines at suitable points in the line circuit 4. In addition, one or more regulating devices can be provided (also not shown in the FIGURE) in order to regulate the respective heat output supplied by the first and/or the second heating device according to the need for heating the reaction medium in the reactor 1.

A further variant, not shown in the FIGURE, comprises a device in which the reactor inlet flow 3 can be preheated, vaporized and overheated by means of the heat content of the flow 4, wherein these options do not necessarily have to be implemented, but can be implemented in any combination.

LIST OF REFERENCE NUMBERS

1 reactor
2 reactor inlet flow
3 reactor outlet flow
4 heat carrier medium circuit flow
5 circulating pump
6 first heating device
7 second heating device operated via waste heat

The invention claimed is:

1. A method for producing vinyl chloride by catalytic thermal cleavage of 1,2-dichloroethane, in which heat required for thermal cleavage is supplied via a liquid or condensing heat transfer medium, wherein the heat transfer medium is at least temporarily and/or at least partially or completely heated by a waste heat from a plant for the incineration of liquid and/or gaseous residues from a chemical plant, wherein at least one first heating device operated by combustion of at least one fuel and additionally at least one second heating device operated via waste heat are utilized to heat the liquid heat transfer medium.

2. The method according to claim 1, wherein the 1,2-dichloroethane is preheated and/or evaporated and/or overheated by the heat transfer medium.

3. The method according to claim 1, wherein the heat transfer medium is heated at least temporarily and/or at least partially by the combustion of at least one fuel and partially by heating it via waste heat.

4. The method according to claim 1, wherein at least one first heating device operated by combustion of at least one fuel and additionally at least one second heating device operated via waste heat are utilized to heat the liquid heat transfer medium.

5. The method according to claim 1, wherein at least one first heating device and at least one second heating device operated via waste heat are connected in series in the circuit.

6. The method according to claim 1, wherein the heat transfer medium is conducted in a circuit into which a reactor is integrated, in which the catalytic thermal cleavage of 1,2-dichloroethane is carried out, wherein a heat exchange takes place between the reaction medium of the reactor and the heat transfer medium.

7. The method according to claim 6, wherein the heat transfer medium is conveyed in the circuit in countercurrent to the flow of the reaction medium through the reactor.

8. The method according to claim 5, wherein the second heating device operated via waste heat is operated at least temporarily by energy obtained from the waste heat from a plant for producing vinyl chloride.

9. The method according to claim 1, wherein the thermal cleavage of the 1,2-dichloroethane is carried out in a temperature range from 200° C. to 400° C.

10. A plant for producing vinyl chloride by catalytic thermal cleavage of 1,2-dichloroethane, in which heat required for preheating, evaporation, overheating and thermal cleavage of 1,2-dichloroethane is supplied via a liquid or condensing heat transfer medium, comprising at least one reactor in which the thermal cleavage takes place and at least one first heating device by which the reaction medium in the reactor is heated by the heat transfer medium, wherein the system further comprises at least one second heating device operated by waste heat from a plant for the incineration of liquid and/or gaseous residues of a chemical plant for heating the reaction medium, wherein the reactor is integrated into a circuit of the heat transfer medium, wherein additionally the at least one first heating device operated via a fuel and further the at least one second heating device operated by means of waste heat are integrated into the circuit of the heat transfer medium.

11. The plant according to claim 10, wherein the circuit of the heat transfer medium comprises a pump integrated into a line system, at least one first heating device operated via a fuel, at least one second heating device operated by waste heat, and the reactor, wherein provisions are made for transferring heat from the heat transfer medium to a reaction medium flowing through the reactor.

12. The plant according to claim 10, wherein the first heating device operated via a fuel and the second heating device operated by waste heat are arranged in series or in parallel in the circuit of the heat transfer medium.

13. The plant according to claim 10, wherein the reactor comprises a tube bundle heat exchanger in which the tubes are filled with catalyst.

14. The plant according to claim 13, wherein the heat transfer medium flows through a jacket space of the reactor in a circuit.

15. The plant according to claim 10, wherein at least one device for preheating and/or evaporating and/or overheating of the 1,2-dichloroethane is integrated into the circuit of the heat transfer medium.

\* \* \* \* \*